United States Patent
Nishide

(10) Patent No.: US 7,099,503 B2
(45) Date of Patent: Aug. 29, 2006

(54) IMAGE RECONSTRUCTION METHOD AND X-RAY CT APPARATUS

(75) Inventor: Akihiko Nishide, Tokyo (JP)

(73) Assignee: GE Medical Systems Global Technology LLC, Waukesha, WI (US)

( * ) Notice: Subject to any disclaimer, the term of this patent is extended or adjusted under 35 U.S.C. 154(b) by 704 days.

(21) Appl. No.: 10/244,287

(22) Filed: Sep. 16, 2002

(65) Prior Publication Data

US 2003/0063786 A1   Apr. 3, 2003

(30) Foreign Application Priority Data

Sep. 17, 2001   (JP)   ............................. 2001-281732

(51) Int. Cl.
*G06K 9/00*   (2006.01)

(52) U.S. Cl. ..................... 382/131; 382/254; 382/285; 250/264; 250/269.1; 250/363.04; 378/4; 378/62

(58) Field of Classification Search ................ 382/128, 382/131, 132, 254, 284–285, 289; 250/261–268, 250/269.1–269.8, 363.04; 378/1, 4, 9, 11, 378/20–27, 55, 62

See application file for complete search history.

(56) References Cited

U.S. PATENT DOCUMENTS

| | | |
|---|---|---|
| 5,416,815 A | 5/1995 | Hsieh |
| 5,515,409 A | 5/1996 | Hsieh |
| 5,610,964 A | 3/1997 | Flohr et al. |
| 5,727,041 A | 3/1998 | Hsieh |
| 5,812,628 A | 9/1998 | Hsieh |
| 6,035,012 A | 3/2000 | Hsieh |
| 6,061,419 A | 5/2000 | Hsieh et al. |
| 6,061,420 A | 5/2000 | Strong et al. |
| 6,115,487 A | 9/2000 | Toth et al. |
| 6,134,292 A | 10/2000 | Hsieh |
| 6,215,841 B1 | 4/2001 | Hsieh |
| 6,233,308 B1 | 5/2001 | Hsieh |
| 6,421,411 B1 | 7/2002 | Hsieh |

*Primary Examiner*—Bhavesh M. Mehta
*Assistant Examiner*—Manav Seth

(74) *Attorney, Agent, or Firm*—Carl B. Horton, Esq.; Armstrong Teasdale LLP

(57) ABSTRACT

For the purpose of reducing artifacts caused by a scan plane tilted with respect to a rotation plane when a multi-row detector is employed, a j-th detector row which an X-ray passing through a pixel point g(x, y) enters is selected based on the distance $\Delta z$ from a scan center plane to an image reconstruction plane in a z-axis direction and the position (x, y) of the pixel point g in the image reconstruction plane, and data of the j-th detector row is used to determine the pixel value of the pixel point g, where the scan center plane at a certain view angle is defined as an x-y plane, and a direction normal to the x-y plane, i.e., a detector row direction, is defined as the z-axis direction.

16 Claims, 4 Drawing Sheets

IMAGE RECONSTRUCTION METHOD AND X-RAY CT APPARATUS

CROSS REFERENCE TO RELATED APPLICATIONS

This application claims the benefit of Japanese Application No. 2001-281732 filed Sep. 17, 2001.

BACKGROUND OF THE INVENTION

The present invention relates to an image reconstruction method and X-ray CT (computed tomography) apparatus, and more particularly to an image reconstruction method and X-ray CT apparatus capable of providing an image reduced in artifacts caused by a scan plane tilted with respect to a rotation plane when a multi-row detector is employed.

FIG. 6 is an prior art diagram showing an image reconstruction method described in Japanese Patent Application Laid Open No. H8-187241.

An X-ray tube 11 and an X-ray detector 53 rotate around a center of rotation IC to collect data at different view angles. The scan plane is defined as an x-y plane.

Image production is basically conducted as follows:
(0) The pixel values for all pixel points g(x, y) in an image reconstruction plane are initialized to zero;
(1) A channel i is determined which detects an X-ray passing through a pixel point g(x, y) in the image reconstruction plane P at a view angle β;
(2) Data of the channel i is added to the pixel value of the pixel point g(x, y);
(3) (1) and (2) are repeated for each view angle β within a required angular range (e.g., 360°) to obtain the pixel value for the pixel point g(x, y); and
(4) (0)–(3) are repeated for every pixel point g(x, y) in the image reconstruction plane P.

The channel i can be uniquely determined once an angle γ that the X-ray passing through the pixel point g(x, y) forms with a center axis Bc of the X-ray beam is known.

The angle γ can be calculated by the following equation:

$$\gamma = \arctan\left\{\frac{t}{D+s}\right\},$$

where
s=x·cos β−y·sin β, and
t=x·sin β−y·cos β where x, y, β, s and t are positive in a direction indicated by arrows shown in FIG. 6; the distance from the X-ray tube 11 to the center of rotation IC is represented by D; s denotes the distance from the foot of the perpendicular dropped from the pixel point g toward the center axis Bc of the X-ray beam, to the center of rotation; and t denotes the length of the perpendicular dropped from the pixel point g toward the center axis Bc of the X-ray beam.

FIG. 7 is an explanatory diagram showing which detector row the X-ray passing through the pixel point g(x, y) enters when a multi-row detector 13 having more than one detector row is employed. The direction normal to the x-y plane, i.e., a detector row direction, is referred to as a z-axis direction. It should be noted that FIG. 7 is a view from a direction orthogonal to the center axis Bc of the X-ray beam.

The larger the width of the multi-row detector 13 in the z-axis direction, i.e., in the row direction, the greater the tilt of the scan plane with respect to the rotation plane.

Conventionally, the tilt is ignored and an image of the image reconstruction plane P is produced by selecting an m-th detector row corresponding to the z-axis position of the image reconstruction plane P and using data of the m-th detector row.

However, the X-ray passing through the pixel point g(x, y) shown in FIG. 7 enters a j-th detector row, instead of the m-th detector row. Thus, there has been a problem that this results in artifacts.

That is, there has been a problem that artifacts (cone angle artifacts) appear which are caused by a scan plane tilted with respect to the rotation plane when a multi-row detector is employed.

SUMMARY OF THE INVENTION

It is therefore an object of the present invention is to provide an image reconstruction method and X-ray CT apparatus capable of providing an image reduced in artifacts caused by a scan plane tilted with respect to a rotation plane when a multi-row detector is employed.

In accordance with its first aspect, the present invention provides an image reconstruction method for reconstructing an image of a specified image reconstruction plane based on data collected at different view angles while rotating at least one of an X-ray tube and a multi-row detector having first—J-th (J≧2) detector rows around a center of rotation, characterized in comprising: selecting a detector row which an X-ray passing through a pixel point g(x, y) enters based on a distance Δz from a scan center plane to an image reconstruction plane in a z-axis direction and a position (x, y) of the pixel point g in the image reconstruction plane; and using data of said detector row to determine a pixel value of said pixel point g, where the scan center plane at a certain view angle is defined as an x-y plane, and a direction normal to said x-y plane, i.e., a detector row direction, is defined as the z-axis direction.

In this configuration, the scan center plane is defined as the central scan plane that contains the center axis Bc of the X-ray beam and extends in the channel direction.

According to the image reconstruction method of the first aspect, the detector row which the X-ray passing through the pixel point g(x, y) actually enters is determined based on the distance Δz from the scan center plane to the image reconstruction plane in the z-axis direction and the position (x, y) of the pixel point g in the image reconstruction plane; and data of the detector row is used to determine the pixel value of the pixel point g. Therefore, it is possible to reduce artifacts caused by the scan plane tilted with respect to the rotation plane when the multi-row detector is employed.

In accordance with its second aspect, the present invention provides the image reconstruction method having the aforesaid configuration, characterized in selecting a j-th detector row determined by:

$$j = rup\left\{\frac{H}{\Delta d} + \frac{J}{2}\right\} \text{ or}$$

$$j = rdwn\left\{\frac{H}{\Delta d} + \frac{J}{2}\right\},$$

where $$\alpha = \arctan\left\{\frac{\Delta z}{D+s}\right\} \text{ and}$$

$$H = fdd \cdot \tan\alpha,$$

where the distance from the X-ray tube to the center of rotation is represented by D, the distance from the X-ray tube to the multi-row detector is represented by fdd, the distance from the foot of the perpendicular dropped from the pixel point g toward a center axis Bc of an X-ray beam, to the center of rotation is represented by s, the length of one detector row in the z-axis direction is represented by Δd, and rup{} denotes a round-up integerization function and rdwn{} denotes a round-down integerization function.

According to the image reconstruction method of the second aspect, the j-th detector row which the X-ray passing through the pixel point g(x, y) actually enters can be suitably determined.

Additionally, $$j = rup\left\{\frac{H}{\Delta d} + \frac{J}{2}\right\}$$

is used when J is odd, and when J is even and H is positive, and $$j = rdwn\left\{\frac{H}{\Delta d} + \frac{J}{2}\right\}$$

is used when J is even and H is negative.

In accordance with its third aspect, the present invention provides the image reconstruction method having the aforesaid configuration, characterized in selecting the j-th detector row and a proximate detector row, and using data obtained by performing an interpolation operation on data of the selected detector rows.

The X-ray passing through the pixel point g(x, y) has a certain extent, and it enters not only the j-th detector row but also a proximate detector row(s).

Therefore, according to the image reconstruction method of the third aspect, data obtained by combining data of those detector rows through an interpolation operation is used to determine the pixel value of the pixel point g. This further reduces artifacts.

In accordance with its fourth aspect, the present invention provides the image reconstruction method having the aforesaid configuration, characterized in selecting the j-th detector row and a (j−1)-th or (j+1)-th detector row, and using data obtained by performing a linear interpolation operation on data of the selected detector rows.

According to the image reconstruction method of the fourth aspect, since a linear interpolation operation is employed, the interpolation operation processing is simple compared to other embodiments described herein.

In accordance with its fifth aspect, the present invention provides the image reconstruction method having the aforesaid configuration, characterized in making j=J when j>1, and making j=1 when j<1.

According to the image reconstruction method of the fifth aspect, if the X-ray passing through the pixel point g(x, y) travels outside a first or second end of the multi-row detector in the row direction, the detector row at the first or second end is selected. Thus, reconstructable data having the least error can be used.

In accordance with its sixth aspect, the present invention provides the image reconstruction method having the aforesaid configuration, characterized in changing the distance Δz from the scan center plane to the image reconstruction plane in the z-axis direction according to the view angle in helical scanning.

In helical scanning, the table moves relative to the gantry, and hence, the position of the scan center plane moves in the z-axis direction according to the view angle.

Therefore, according to the image reconstruction method of the sixth aspect, the distance Δz is gradually changed by an amount equal to the distance of the table movement for each view angle. Thus, the detector row which an X-ray passing through the pixel point g(x, y) enters can be accurately determined even in helical scanning.

In accordance with its seventh aspect, the present invention provides the image reconstruction method having the aforesaid configuration, characterized in applying a weight inversely proportional to $\{(D+s)^2+t^2\}$ to data of the selected detector rows for each view angle, and adding the weighted data to determine the pixel value of the pixel point g, where the distance from the X-ray tube to the center of rotation is represented by D, the distance from the foot of the perpendicular dropped from the pixel point g toward the center axis Bc of the X-ray beam, to the center of rotation is represented by s, and the length of the perpendicular dropped from the pixel point g toward the center axis Bc of the X-ray beam is represented by t.

An X-ray emitted by the X-ray tube passes through a pixel point close to the X-ray tube and thereafter a pixel point far from the X-ray tube and reaches the X-ray detector. In this case, the pixel point close to the X-ray tube affects data more than that far from the X-ray tube does.

Therefore, according to the image reconstruction method of the seventh aspect, data is added with a weight in inverse proportional to the square of the distance from the X-ray tube to the pixel point. Thus, a more natural image can be produced.

In accordance with its eighth aspect, the present invention provides the image reconstruction method having the aforesaid configuration, characterized in selecting a channel from which the data for use in determining the pixel value of said pixel point g is obtained, based on the view angle and the position (x, y) of the pixel point g in the image reconstruction plane.

According to the image reconstruction method of the eighth aspect, the channel which the X-ray passing through the pixel point g(x, y) actually enters can be selected.

In accordance with its ninth aspect, the present invention provides an X-ray CT apparatus comprising an X-ray tube, a multi-row detector having first—J-th (J≧2) detector rows, and data collecting means for collecting data at different view angles while rotating at least one of said X-ray tube and said multi-row detector around a center of rotation, characterized in further comprising: detector row selecting means for selecting a detector row based on a distance Δz from a scan center plane to a specified image reconstruction plane in a z-axis direction and a position (x, y) of the pixel point g in the image reconstruction plane, where the scan center plane at a certain view angle is defined as an x-y plane, and a direction normal to said x-y plane, i.e., a detector row direction, is defined as the z-axis direction; and image producing means for reconstructing an image of the image reconstruction plane by adding data of the selected detector row for each view angle to determine a pixel value of said pixel point g.

According to the X-ray CT apparatus of the ninth aspect, the image reconstruction method as described regarding the first aspect can be suitably implemented.

In accordance with its tenth aspect, the present invention provides the X-ray CT apparatus having the aforesaid configuration, characterized in that said detector row selecting means selects a j-th detector row determined by:

$$j = rup\left\{\frac{H}{\Delta d} + \frac{J}{2}\right\} \text{ or}$$

$$j = rdwn\left\{\frac{H}{\Delta d} + \frac{J}{2}\right\},$$

where $$\alpha = \arctan\left\{\frac{\Delta z}{D+s}\right\} \text{ and}$$

$$H = fdd \cdot \tan\alpha,$$

where the distance from the X-ray tube to the center of rotation is represented by D, the distance from the X-ray tube to the multi-row detector is represented by fdd, the distance from the foot of the perpendicular dropped from the pixel point g toward a center axis Bc of an X-ray beam, to the center of rotation is represented by s, the length of one detector row in the z-axis direction is represented by $\Delta d$, and rup{} denotes a round-up integerization function and rdwn{} denotes a round-down integerization function.

According to the X-ray CT apparatus of the tenth aspect, the image reconstruction method as described regarding the second aspect can be suitably implemented.

In accordance with its eleventh aspect, the present invention provides the X-ray CT apparatus having the aforesaid configuration, characterized in that said detector row selecting means selects the j-th detector row and a proximate detector row, and said image producing means uses data obtained by performing an interpolation operation on data of the selected detector rows.

According to the X-ray CT apparatus of the eleventh aspect, the image reconstruction method as described regarding the third aspect can be suitably implemented.

In accordance with its twelfth aspect, the present invention provides the X-ray CT apparatus having the aforesaid configuration, characterized in that said detector row selecting means selects the j-th detector row and a (j−1)-th or (j+1)-th detector row, and said image producing means uses data obtained by performing a linear interpolation operation on data of the selected detector rows.

According to the X-ray CT apparatus of the twelfth aspect, the image reconstruction method as described regarding the fourth aspect can be suitably implemented.

In accordance with its thirteenth aspect, the present invention provides the X-ray CT apparatus having the aforesaid configuration, characterized in that said detector row selecting means makes j=J when j>J, and makes j=1 when j<1.

According to the X-ray CT apparatus of the thirteenth aspect, the image reconstruction method as described regarding the fifth aspect can be suitably implemented.

In accordance with its fourteenth aspect, the present invention provides the X-ray CT apparatus having the aforesaid configuration, characterized in that said detector row selecting means changes the distance $\Delta z$ from the scan center plane to the image reconstruction plane in the z-axis direction according to the view angle in helical scanning.

According to the X-ray CT apparatus of the fourteenth aspect, the image reconstruction method as described regarding the sixth aspect can be suitably implemented.

In accordance with its fifteenth aspect, the present invention provides the X-ray CT apparatus having the aforesaid configuration, characterized in that said image producing means applies a weight inversely proportional to $\{(D+s)^2 + t^2\}$ to the data of the selected detector rows for each view angle, and adds the weighted data to determine the pixel value of the pixel point g, where the distance from the X-ray tube to the center of rotation is represented by D, the distance from the foot of the perpendicular dropped from the pixel point g toward the center axis Bc of the X-ray beam, to the center of rotation is represented by s, and the length of the perpendicular dropped from the pixel point g toward the center axis Bc of the X-ray beam is represented by t.

According to the X-ray CT apparatus of the fifteenth aspect, the image reconstruction method as described regarding the seventh aspect can be suitably implemented.

In accordance with its sixteenth aspect, the present invention provides the X-ray CT apparatus having the aforesaid configuration, characterized in comprising channel selecting means for selecting a channel from which the data for use in determining the pixel value of said pixel point g is obtained, based on the view angle and the position (x, y) of the pixel point g in the image reconstruction plane.

According to the X-ray CT apparatus of the sixteenth aspect, the image reconstruction method as described regarding the eighth aspect can be suitably implemented.

According to the image reconstruction method and X-ray CT apparatus of the present invention, it is possible to reduce artifacts caused by a scan plane tilted with respect to a rotation plane when a multi-row detector is employed.

Further objects and advantages of the present invention will be apparent from the following description of the preferred embodiments of the invention as illustrated in the accompanying drawings.

DETAILED DESCRIPTION OF THE INVENTION

Several embodiments of the present invention will now be described with reference to the accompanying drawings.

FIRST EMBODIMENT

Figure 1A:
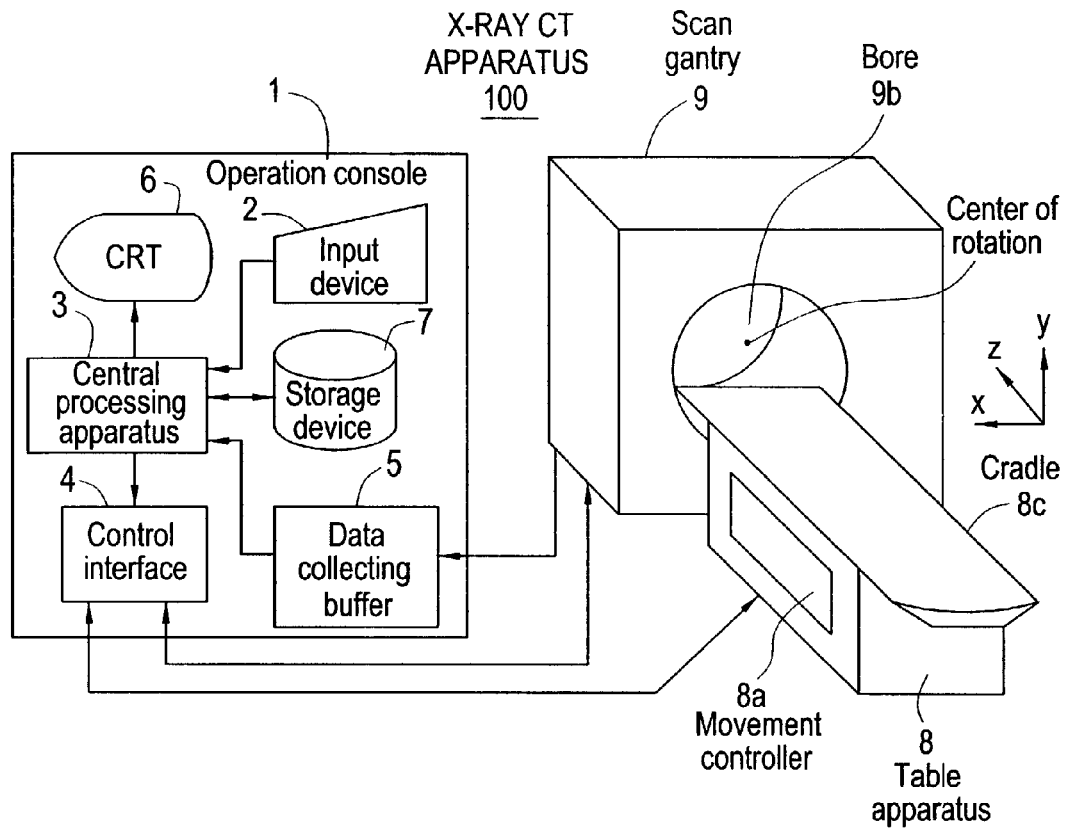
FIG. 1 is a block diagram of an X-ray CT apparatus in accordance with a first embodiment.
Figure 1B:
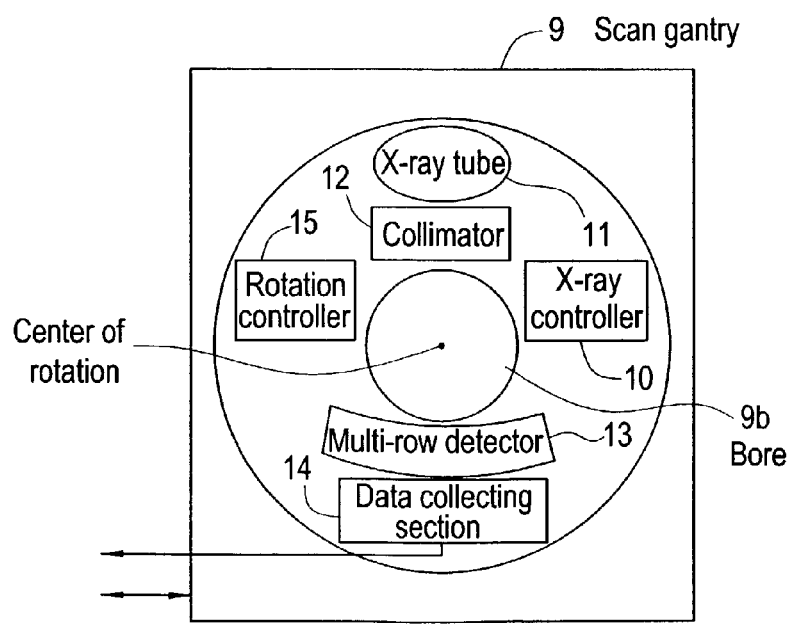

FIG. 1 is a block diagram of an X-ray CT apparatus 100 in accordance with a first embodiment of the present invention.

The X-ray CT apparatus 100 comprises an operation console 1, a table apparatus 8 and a scan gantry 9.

The operation console 1 comprises an input device 2 for receiving commands and information input by an operator, a central processing apparatus 3 for executing scan processing and image reconstruction processing, a control interface 4 for communicating control signals etc. with the imaging table 8 and scan gantry 9, a data collection buffer 5 for collecting data acquired by the scan gantry 9, a CRT 6 for displaying an image reconstructed from the data, and a storage device 7 for storing programs, data and images.

The table apparatus 8 comprises a cradle 8c for resting a subject, and a movement controller 8a for moving the cradle 8c in z- and y-axis directions.

The y-axis represents the vertical direction, and the z-axis represents the longitudinal direction of the cradle 8c. Moreover, an axis orthogonal to the y- and z-axes is defined as an x-axis. The subject's body axis extends along the z-axis direction.

The scan gantry 9 comprises an X-ray controller 10, an X-ray tube 11, a collimator 12, a multi-row detector 13 having more than one detector row, a data collecting section 14, and a rotation controller 15 for rotating the X-ray tube 11 and multi-row detector 13 etc. around a center of rotation IC.

Figure 2:
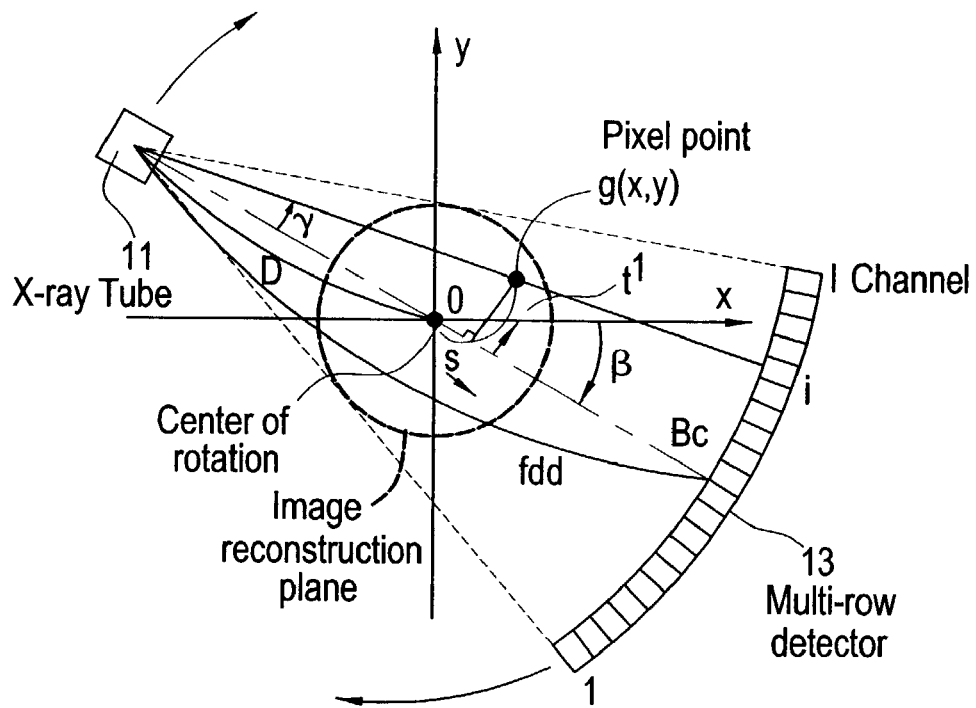
FIG. 2 is an explanatory diagram of image reconstruction processing (as viewed from a z-axis direction) in accordance with the first embodiment.
Figure 3:
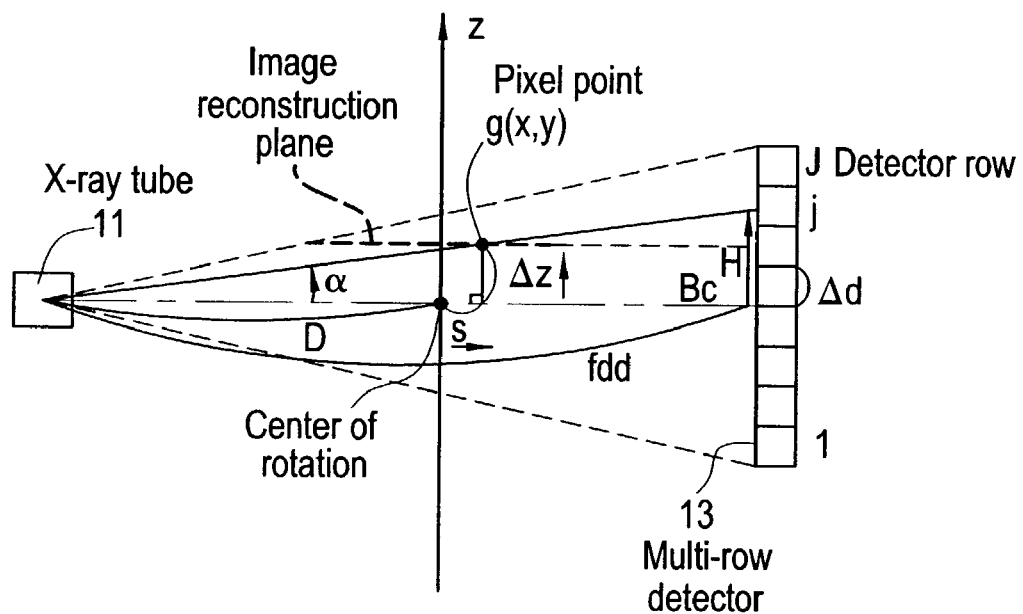
FIG. 3 is an explanatory diagram of the image reconstruction processing (as viewed from a direction orthogonal to the z-axis and X-ray beam center axis) in accordance with the first embodiment.

FIGS. 2 and 3 are explanatory diagrams showing an image reconstruction method in accordance with the first embodiment of the present invention.

FIG. 2 is a view from the z-axis direction. The X-ray tube 11 and multi-row detector 13 rotate around the center of rotation IC to collect data from different view angles.

FIG. 3 is a view from a direction orthogonal to the z-axis and the center axis Bc of the X-ray beam. The multi-row detector 13 has first—J-th (J≧2) detector rows in the z-axis direction.

The scan plane is tilted with respect to the rotation plane. A central scan plane that contains the center axis Bc of the X-ray beam and extends in the channel direction will be referred to as a scan center plane. The scan center plane coincides with the rotation plane, and is in the x-y plane.

Image production is basically conducted as follows:

(0) The pixel values for all pixel points g(x, y) in an image reconstruction plane are initialized to zero;
(1) A channel i is determined which detects an X-ray passing through a pixel point g(x, y) in the image reconstruction plane P at a view angle β, as shown in FIG. 2;
(2) A j-th detector row is determined which detects the X-ray passing through the pixel point g(x, y) in the image reconstruction plane P, as shown in FIG. 3;
(3) A weight W is calculated for data of the channel i in the j-th detector row;
(4) The data of the channel i in the j-th detector row is multiplied by the weight W, and the weighted data is added to the pixel value of the pixel point g(x, y);
(5) (1)–(4) are repeated for each view angle β within a required angular range (e.g., 360°) to obtain the pixel value of the pixel point g(x, y); and
(6) (0)–(5) are repeated for every pixel point g(x, y) in the image reconstruction plane P.

In (1), the channel i can be uniquely determined once an angle γ which the X-ray passing through the pixel point g(x, y) forms with the center axis Bc of the X-ray beam is known, as can be seen from FIG. 2.

The angle γ can be calculated by the following equation:

$$\gamma = \arctan\left\{\frac{t'}{D+s}\right\},$$

where s = x·cos β − y·sin β, and t' = x·sin β − y·cos β, where x, y, β, s and t' are positive in a direction indicated by arrows shown in FIG. 2; the distance from the X-ray tube 11 to the center of rotation IC is represented by D; s denotes the distance from the foot of the perpendicular dropped from the pixel point g toward the center axis Bc of the X-ray beam, to the center of rotation; and t' denotes the length of the projection of the perpendicular dropped from the pixel point g toward the center axis Bc of the X-ray beam, onto the scan center plane.

In (2), the j-th detector row can be uniquely determined when an angle α which the X-ray passing through the pixel point g(x, y) forms with the center axis Bc of the X-ray beam is known, as can be seen from FIG. 3.

The angle α can be calculated by the following equation:

$$\alpha = \arctan\left\{\frac{\Delta z}{D+s}\right\},$$

where s and Δz are positive in a direction indicated by arrows shown in FIG. 3; and Δz denotes the distance from the scan center plane to the image reconstruction plane in the z-axis direction.

Now j can be determined by:

$$j = rup\left\{\frac{H}{\Delta d} + \frac{J}{2}\right\} \text{ or}$$

$$j = rdwn\left\{\frac{H}{\Delta d} + \frac{J}{2}\right\},$$

where

H = fdd · tan α, where the distance from the X-ray tube 11 to the multi-row detector 13 is represented by fdd, the length of one detector row in the z-axis direction is represented by Δd, and rup{ } denotes a round-up integerization function and rdwn{ } denotes a round-down integerization function.

$$j = rup\left\{\frac{H}{\Delta d} + \frac{J}{2}\right\}$$

is used when J is odd, and when J is even and H is positive, and $$j = rdwn\left\{\frac{H}{\Delta d} + \frac{J}{2}\right\}$$

is used when J is even and H is negative.

In helical scanning, while the position of the image reconstruction plane P is not changed, the position of the scan center plane is moved according to the view angle. Therefore, Δz should be changed with the view angle.

According to the X-ray CT apparatus 100 of the first embodiment, a j-th detector row and a channel i which an X-ray passing through a pixel point g actually enters are determined, and the data of the j-th detector row and channel i is used to determine the pixel value of the pixel point g. Thus, it is possible to reduce artifacts caused by a scan plane tilted with respect to a rotation plane when the multi-row detector 13 is employed.

SECOND EMBODIMENT

In a second embodiment, not only data of the j-th detector row but also data of a proximate detector row are employed, and an image is reconstructed from data obtained by performing a linear interpolation operation on those data.

Figure 4:
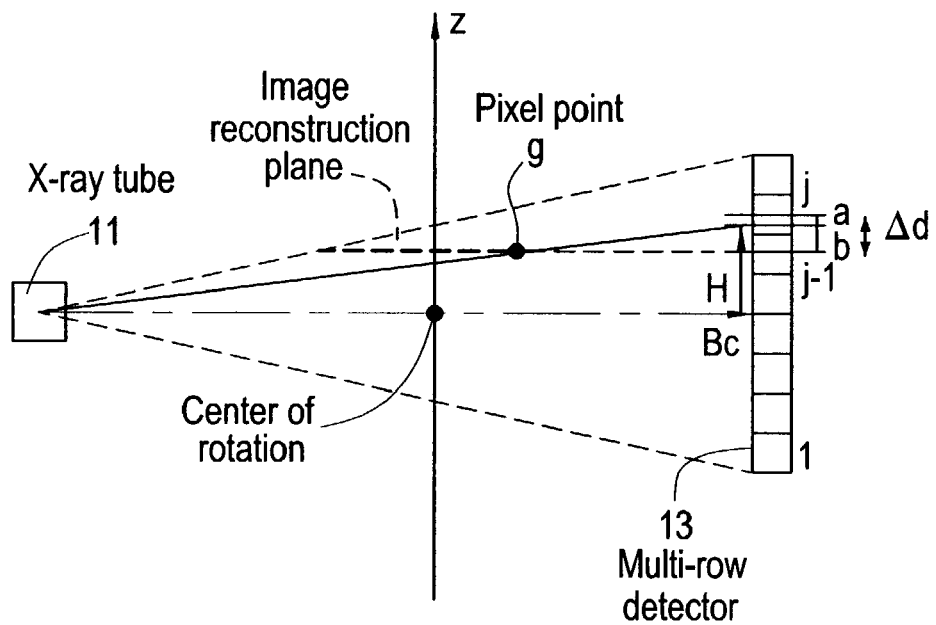
FIG. 4 is an explanatory diagram of image reconstruction processing (as viewed from a direction orthogonal to the z-axis and X-ray beam center axis) in accordance with a second embodiment.

As shown in FIG. 4, first, a j-th detector is selected, as in the first embodiment.

If the j-th detector is selected by $$j = rup\left\{\frac{H}{\Delta d} + \frac{J}{2}\right\}, \text{ and } \frac{H}{\Delta d} - rdwn\left\{\frac{H}{\Delta d}\right\} \leq 0.5,$$

a (j−1)-th detector row is selected. Then, representing data of the j-th detector and channel i by d(j, i) and data of the (j−1)-th detector and channel i by d(j−1, i), data d obtained by a linear interpolation operation:

$d = a \cdot d(j-1, i) + b \cdot d(j, i)$, where $$a = 0.5 - \frac{H}{\Delta d} - rdwn\left\{\frac{H}{\Delta d}\right\}, \text{ and}$$
$$b = 1 - a,$$

is multiplied by a weight W, and the weighted data is added to the pixel value of the pixel point g.

Moreover, if the j-th detector is selected by $$j = rup\left\{\frac{H}{\Delta d} + \frac{J}{2}\right\}, \text{ and } \frac{H}{\Delta d} - rdwn\left\{\frac{H}{\Delta d}\right\} > 0.5,$$

a (j+1)-th detector row is selected. Then, representing data of the j-th detector and channel i by d(j, i) and data of the (j+1)-th detector and channel i by d(j+1, i), data d obtained by a linear interpolation operation:

$d = a \cdot d(j+1, i) + b \cdot d(j, i)$, where $$a = \frac{H}{\Delta d} - rdwn\left\{\frac{H}{\Delta d}\right\} - 0.5, \text{ and}$$
$$b = 1 - a,$$

is multiplied by a weight W, and the weighted data is added to the pixel value of the pixel point g.

On the other hand, if the j-th detector is selected by $$j = rdown\left\{\frac{H}{\Delta d} + \frac{J}{2}\right\}, \text{ and } \frac{H}{\Delta d} - rdwn\left\{\frac{H}{\Delta d}\right\} \leq 0.5,$$

a (j−1)-th detector row is selected. Then, representing data of the j-th detector and channel i by d(j, i) and data of the (j−1)-th detector and channel i by (d(j−1, i), data d obtained by linear interpolation operation: $d = a \cdot d(j-1, i) + b \cdot d(j, i)$, where $$a = 0.5 - \frac{H}{\Delta d} - rdwn\left\{\frac{H}{\Delta d}\right\}, \text{ and}$$
$$b = 1 - a,$$

is multiplied by a weight W, and the weighted data is added to the pixel value of the pixel point g.

Moreover, if the j-th detector is selected by $$j = rdwn\left\{\frac{H}{\Delta d} + \frac{J}{2}\right\}, \text{ and } \frac{H}{\Delta d} - rdwn\left\{\frac{H}{\Delta d}\right\} > 0.5,$$

a (j+1)-th detector row is selected. Then, representing data of the j-th detector and channel i by (j, i) and data of the (j+1)-th detector and channel i by d(j+1, i), data d obtained by a linear interpolation operation:

$d = a \cdot d(j+1, i) + b \cdot d(j, i)$, where $$a = \frac{H}{\Delta d} - rdwn\left\{\frac{H}{\Delta d}\right\} - 0.5, \text{ and}$$
$$b = 1 - a,$$

is multiplied by a weight W, and the weighted data is added to the pixel value of the pixel point g.

According to the X-ray CT apparatus of the second embodiment, artifacts can be reduced more than in the first embodiment.

Preferably, the linear interpolation is performed also in the channel direction, i.e., on data of a channel i and data of a channel (i−1) or (i+1).

THIRD EMBODIMENT

Instead of the linear interpolation operation, two-dimensional Hanning interpolation may be performed in a detector row direction and a channel direction. Alternatively, cubic interpolation or Lagrange interpolation may be performed. Although operation processing is complicated in such interpolation, an image of good quality can be obtained, as compared with the linear interpolation operation.

FOURTH EMBODIMENT

Figure 5:
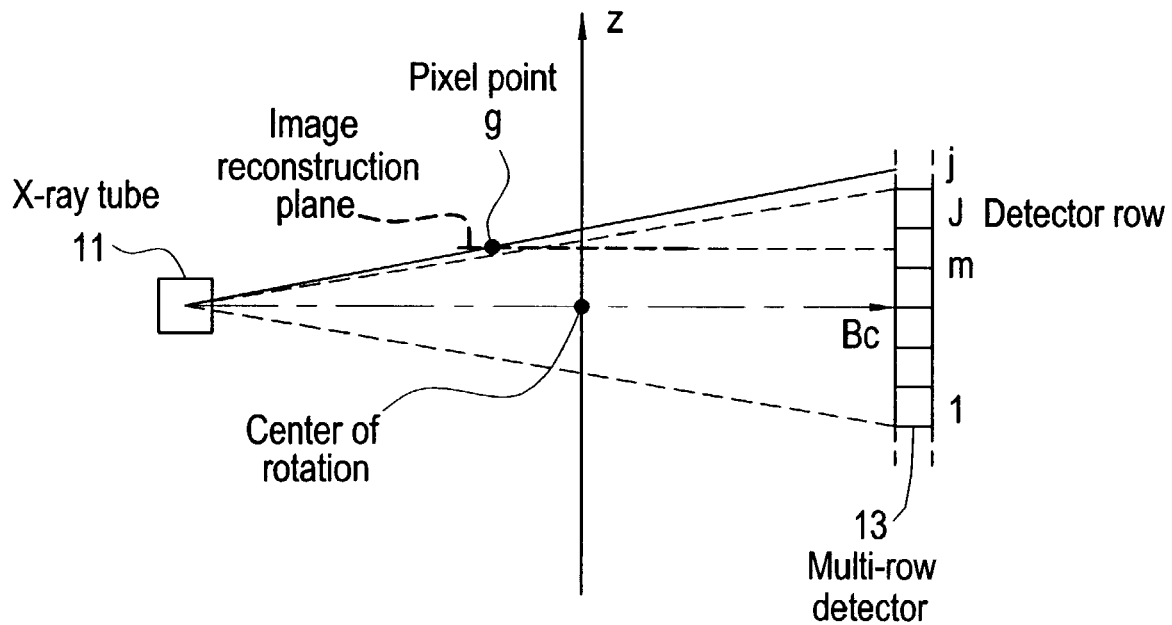
FIG. 5 is an explanatory diagram of image reconstruction processing (as viewed from a direction orthogonal to the z-axis and X-ray beam center axis) in accordance with a fourth embodiment.
Figure 6:
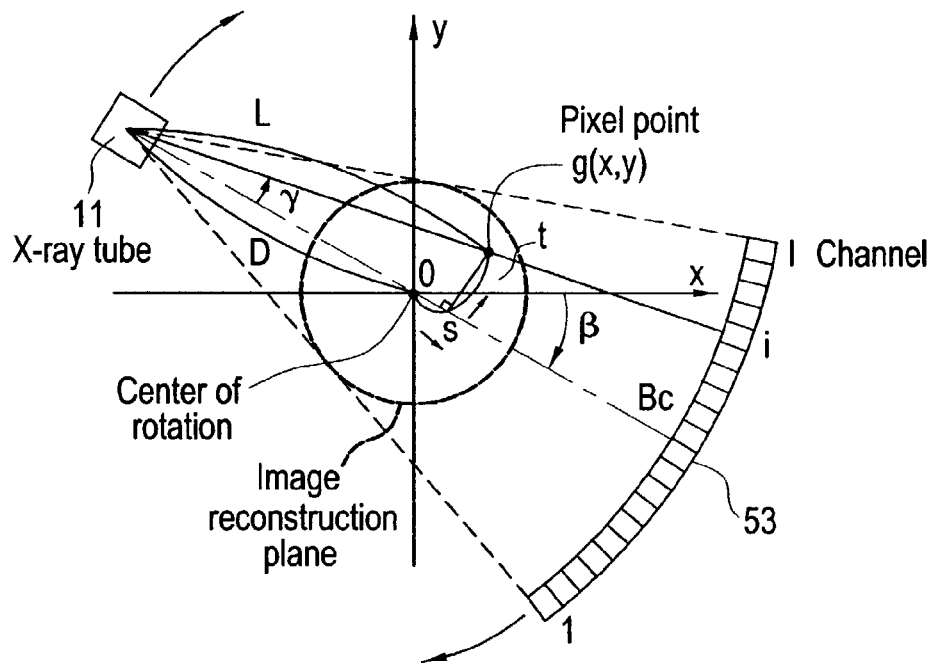
FIG. 6 is an explanatory diagram of conventional image reconstruction processing (as viewed from the z-axis direction).
Figure 7:
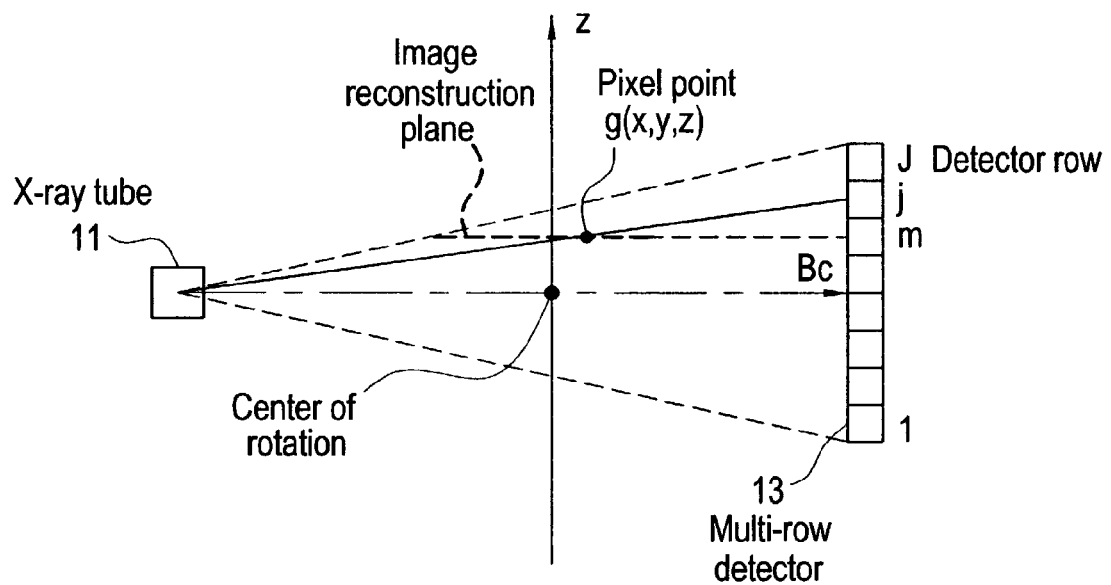
FIG. 7 is a diagram explaining an object of the present invention (as viewed from a direction orthogonal to the z-axis and X-ray beam center axis).

As shown in FIG. 5, if j>J, then j is made j=J to select a J-th detector row.

If j<1, then j is made j=1 to select a first detector row.

According to the image reconstruction method of the fourth aspect, even if an X-ray passing through a pixel point g travels outside a first or second end of the multi-row detector 13, most suitable data possible can be used.

Many widely different embodiments of the invention may be constructed without departing from the spirit and the scope of the present invention. It should be understood that the present invention is not limited to the specific embodiments described in the specification, except as defined in the appended claims.

The invention claimed is:

1. An image reconstruction method for reconstructing an image of a specified image reconstruction plane based on data collected at different view angles while rotating at least one of an X-ray tube and a multi-row detector having first—J-th (J≧2) detector rows around a center of rotation, comprising the steps of:
   selecting a detector row which an X-ray passing through a pixel point g(x, y) enters based on a distance Δz from a scan center plane to an image reconstruction plane in a z-axis direction and a position (x, y) of the pixel point g in the image reconstruction plane; and
   using data of said detector row to determine a pixel value of said pixel point g, where the scan center plane at a certain view angle is defined as an x-y plane, and a direction normal to said x-y plane, i.e., a detector row direction, is defined as the z-axis direction.

2. The image reconstruction method of claim 1, comprising the step of selecting a j-th detector row determined by:

$$j = rup\left\{\frac{H}{\Delta d} + \frac{J}{2}\right\} \text{ or}$$

$$j = rdwn\left\{\frac{H}{\Delta d} + \frac{J}{2}\right\}, \text{ where}$$

$$\alpha = \arctan\left\{\frac{\Delta z}{D+s}\right\} \text{ and}$$

$$H = fdd \cdot \tan\alpha,$$

where the distance from the X-ray tube to the center of rotation is represented by D, the distance from the X-ray tube to the multi-row detector is represented by fdd, the distance from the foot of the perpendicular dropped from the pixel point g toward a center axis Bc of an X-ray beam, to the center of rotation is represented by s, the length of one detector row in the z-axis direction is represented by Δd, and rup{} denotes a round-up integerization function and rdwn{} denotes a round-down integerization function.

3. The image reconstruction method of claim 2, comprising the steps of: selecting the j-th detector row and a proximate detector row; and using data obtained by performing an interpolation operation on data of the selected detector rows.

4. The image reconstruction method of claim 3, comprising the steps of: selecting the j-th detector row and a (j−1)-th or (j+1)-th detector row; and using data obtained by performing a linear interpolation operation on data of the selected detector rows.

5. The image reconstruction method of claim 2, comprising the step of making j=J when j>1, and making j=1 when j<1.

6. The image reconstruction method of claim 1, comprising the step of changing the distance Δz from the scan center plane to the image reconstruction plane in the z-axis direction according to the view angle in helical scanning.

7. The image reconstruction method of claim 1, comprising the steps of: applying a weight inversely proportional to $\{(D+s)^2+t^2\}$ to data of the selected detector rows for each view angle; and adding the weighted data to determine the pixel value of the pixel point g, where the distance from the X-ray tube to the center of rotation is represented by D, the distance from the foot of the perpendicular dropped from the pixel point g toward the center axis Bc of the X-ray beam, to the center of rotation is represented by s, and the length of the perpendicular dropped from the pixel point g toward the center axis Bc of the X-ray beam is represented by t.

8. The image reconstruction method of claim 1, comprising the step of selecting a channel from which the data for use in determining the pixel value of said pixel point g is obtained, based on the view angle and the position (x, y) of the pixel point g in the image reconstruction plane.

9. An X-ray CT apparatus comprising:
   an X-ray tube;
   a multi-row detector having first—J-th (J≧2) detector rows;
   a data collecting device for collecting data at different view angles while rotating at least one of said X-ray tube and said multi-row detector around a center of rotation;
   a detector row selecting device for selecting a detector row which an X-ray passing through a pixel point g(x, y) enters based on a distance Δz from a scan center plane to a specified image reconstruction plane in a z-axis direction and a position (x, y) of the pixel point g in the image reconstruction plane, where the scan center plane at a certain view angle is defined as an x-y plane, and a direction normal to said x-y plane, i.e., a detector row direction, is defined as the z-axis direction; and
   an image producing device for reconstructing an image of the image reconstruction plane by adding data of the selected detector row for each view angle to determine a pixel value of said pixel point g.

10. The X-ray CT apparatus of claim 9, wherein said detector row selecting device selects a j-th detector row determined by:

$$j = rup\left\{\frac{H}{\Delta d} + \frac{J}{2}\right\} \text{ or}$$

$$j = rdwn\left\{\frac{H}{\Delta d} + \frac{J}{2}\right\}, \text{ where}$$

$$\alpha = \arctan\left\{\frac{\Delta z}{D+s}\right\} \text{ and}$$

$$H = fdd \cdot \tan\alpha,$$

where the distance from the X-ray tube to the center of rotation is represented by D, the distance from the X-ray tube to the multi-row detector is represented by fdd, the distance from the foot of the perpendicular dropped from the pixel point g toward a center axis Bc of an X-ray beam, to the center of rotation is represented by s, the length of one detector row in the z-axis direction is represented by Δd, and rup{} denotes a round-up integerization function and rdwn{} denotes a round-down integerization function.

11. The X-ray CT apparatus of claim 10, wherein said detector row selecting device makes j=J when j>1, and makes j=1 when j<1.

12. The X-ray CT apparatus of claim 10, wherein said detector row selecting device selects the j-th detector row and a proximate detector row, and said image producing device uses data obtained by performing an interpolation operation on data of the selected detector rows.

13. The X-ray CT apparatus of claim 12, wherein said detector row selecting device selects the j-th detector row and a (j−1)-th or (j+1)-th detector row, and said image producing device uses data obtained by performing a linear interpolation operation on data of the selected detector rows.

14. The X-ray CT apparatus of claim 9, wherein said detector row selecting device changes the distance Δz from the scan center plane to the image reconstruction plane in the z-axis direction according to the view angle in helical scanning.

15. The X-ray CT apparatus of claim 9, wherein said image producing device applies a weight inversely proportional to $\{(D+s)^2+t^2\}$ to the data of the selected detector rows for each view angle, and adds the weighted data to determine the pixel value of the pixel point g, where the distance from the X-ray tube to the center of rotation is represented by D, the distance from the foot of the perpendicular dropped from the pixel point g toward the center axis Bc of the X-ray beam, to the center of rotation is represented by s, and the length of the perpendicular dropped from the pixel point g toward the center axis Bc of the X-ray beam is represented by t.

16. The X-ray CT apparatus of claim 9, further comprising a channel selecting device for selecting a channel from which the data for use in determining the pixel value of said pixel point g is obtained, based on the view angle and the position (x, y) of the pixel point g in the image reconstruction plane.

* * * * *